United States Patent [19]

Ancel et al.

[11] Patent Number: 5,744,617
[45] Date of Patent: Apr. 28, 1998

[54] PROCESS FOR THE PREPARATION OF SUBSTITUTED PHENOLS

[75] Inventors: Jean-Erick Ancel; Hugues Bienayme, both of Lyons; Pierre Meilland, Chaponost, all of France

[73] Assignee: Rhone-Poulenc Nutrition Animale, Antony Cedex, France

[21] Appl. No.: 644,863

[22] Filed: May 10, 1996

[30] Foreign Application Priority Data

May 10, 1995 [FR] France .................. 95 05509

[51] Int. Cl.$^6$ .................. C07D 311/04; C07C 39/04
[52] U.S. Cl. .................. 549/408; 568/716
[58] Field of Search .................. 549/408, 410, 549/411, 412; 568/794, 716

[56] References Cited

U.S. PATENT DOCUMENTS

| | | | |
|---|---|---|---|
| 3,708,505 | 1/1973 | Greenbaum et al. | 549/408 |
| 4,550,182 | 10/1985 | Ernst et al. | 549/408 |
| 4,594,460 | 6/1986 | Mignani et al. | 568/794 |
| 4,636,570 | 1/1987 | Chabardes et al. | 549/408 |
| 4,639,533 | 1/1987 | Finnan | 549/411 |
| 5,110,955 | 5/1992 | Knierzinger et al. | 549/411 |
| 5,348,869 | 9/1994 | Stocker et al. | 435/125 |
| 5,462,865 | 10/1995 | Stocker et al. | 435/125 |

OTHER PUBLICATIONS

Chemical Abstract, vol. 93, No.17, Abstract No. 168127r, 1993.

Chemical Abstract, vol. 90, No. 23, Abstract No. 187181h, 1990.

*Primary Examiner*—Deborah Lambkin
*Attorney, Agent, or Firm*—Finnegan, Henderson, Farabow, Garrett & Dunner, L.L.P.

[57] ABSTRACT

A process for the preparation of substituted phenols, in particular, the condensation of phenols having one or more alkyl substituents with a butadiene derivative comprising at least six carbon atoms, in particular myrcene and/or β-springene is disclosed. The cyclization, in the form of chromans, of the products obtained during this condensation and their hydrogenation in order to prepare vitamin E is also disclosed.

20 Claims, No Drawings

PROCESS FOR THE PREPARATION OF SUBSTITUTED PHENOLS

The present invention relates to a new process for the preparation of substituted phenols. The present invention more particularly relates to the condensation of phenols carrying one or more alkyl substituents with a butadiene derivative comprising at least six carbon atoms. The present invention also relates to the cyclization, in the form of chromans, of the products obtained from this condensation.

It is known according to U.S. Pat. No. 4,594,460 to condense a phenol substituted with one or more radicals chosen from halogens, hydroxyl groups optionally in ether or ester form, alkyl groups, nitro groups, aldehyde groups optionally in acetal form, acetyl groups, benzyl groups, amino groups, alkylamino groups, dialkylamino groups or alkyloxycarbonyl groups with a butadiene derivative containing 5 to 24 carbon atoms. This condensation is performed, according to U.S. Pat. No. 4,594,460, in the presence of a rhodium-based catalyst and a water-soluble phosphine.

It emerged that when it was desired to apply this reaction to the condensation of a phenol carrying a hydroxyl radical and several methyl radicals, for example to trimethylphenol or to trimethylhydroquinone, with a butadiene derivative comprising at least six carbon atoms, this reaction did not give the expected product. The reproduction of this reaction is included in this application, as comparative example (C4).

It is also known according to the Japanese patent published under the number JP 55-15411 to react a dimethoxyphenol with isoprene in the presence of a rhodium-based catalyst and a triphenylphosphine. When these reaction conditions are applied to the condensation of a butadiene derivative comprising more than six carbon atoms, such as myrcene with trimethylhydroquinone, no reaction product is formed.

Even with the benefit of these two previously mentioned documents relating to the substitution of a phenol with a butadiene derivative, the problem remained with regard to the condensation of a phenol, not activated by several alkoxy groups, with a butadiene derivative comprising at least six carbon atoms.

The present invention has made it possible to achieve this objective, that is, the condensation of a phenol or of a diphenol substituted with at least one alkyl group with a butadiene derivative comprising at least six carbon atoms.

The present invention thus relates to a process for the preparation of substituted phenols of formula (I)

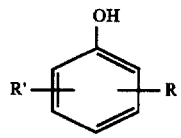

in which R represents one or more groups, which groups are identical or different and are chosen from hydrogen, hydroxyl radicals or alkyl radicals having from 1 to 6 carbon atoms, and R' represents a radical chosen from the radicals of formula (II)

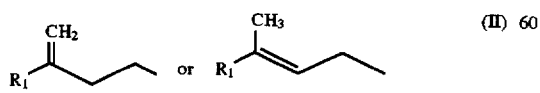

in which $R_1$ represents an optionally substituted alkylene or alkyl radical, and wherein the radical of formula (11) contains at least 6 carbon atoms, which process comprises the step of condensing a phenol of formula (III)

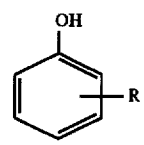

in which R has the same meaning as in formula (I), in a single-phase medium with a butadiene derivative of formula (IV)

in which $R_1$ has the same meaning as in formula (II), in the presence of a base, a diphosphine soluble in an aprotic organic solvent, and a catalyst based on rhodium with the oxidation number (+1).

Among the butadiene derivatives of formula (IV), use of the polyene compounds is preferred, and more preferably, myrcene, springene and farnesene are used. Among the derivatives of formula (III), use of the compounds for which R represents several alkyl radicals is preferred, and most preferably trimethylphenol and trimethylhydroquinone are used.

The rhodium-based reaction catalyst is preferably an organic salt of rhodium having the oxidation number (+1), preferably chosen from [Rh Cl (P($C_6H_5$)$_3$)$_2$]$_2$, Rh Cl (CO) (P($C_6H_5$)$_3$)$_2$ and [Rh Cl (COD)]$_2$. It is evident that a person skilled in the art can use a derivative of rhodium with a higher oxidation number, but will have to add a reducing element before using the catalyst in the reaction envisaged.

The diphosphine soluble in aprotic organic solvent is preferably chosen from bidentate diphosphines having a hydrocarbon chain between the two phosphorus atoms comprising from 3 to 5 carbon atoms. There may be mentioned, among the preferred phosphines, 1,4-bis(diphenylphosphino)butane, 1,3-bis(diphenyl-phosphino)propane, 1,2-bis(diphenylphosphino-methylene)cyclobutane, and 1,5-bis(diphenylphosphino)-pentane. It is more preferable to use 1,4-bis(diphenyl-phosphino)butane of formula:

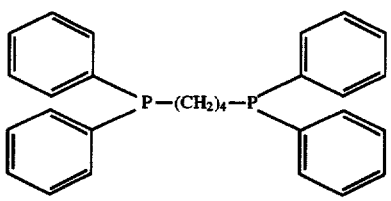

or 1,2-bis(diphosphinomethylene)cyclobutane of formula:

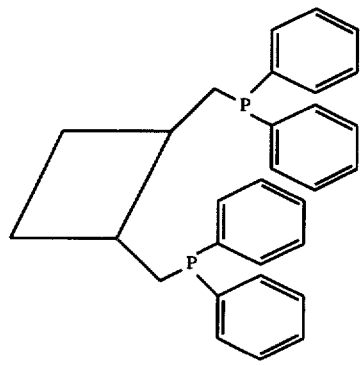

The present invention relates more particularly to the condensation of β-springene or of myrcene with trimethylhydroquinone in the presence of a catalyst based on rhodium with the oxidation number (+1) and of bis(diphenylphosphino)butane or bis(diphenylphosphino)cyclobutane.

According to a more preferred way of carrying out the invention, the molar ratio of the rhodium-based catalyst to the butadiene derivative preferably ranges from 0.1% to 10%. The molar ratio of the butadiene derivative to the phenol preferably ranges from 0.2 to 2.

Any type of solvent can be used, such as water or organic solvents or a mixture of both. According to a more preferred way of carrying out the invention, the solvent used is preferably aprotic, it will thereby solubilize, in particular, the phenol and the butadiene derivative. Thus, aromatic solvents, ethers, ketones and esters can be used within the framework of the present invention. Among these solvents, the use of toluene, dimethoxyethane and isopropyl acetate (IPAC) is more preferred.

To catalyse the reaction, it is advantageous to add a base which is preferably insoluble in the reaction medium. It is thus possible to use alkali metal carbonates such as sodium or potassium carbonates. This base may be added in solid form or in the form of an aqueous solution.

The reaction temperature preferably ranges from 30° C. to 150° C. and the reaction time ranges from a few hours to one day.

According to a second aspect of the invention, the derivative obtained by condensation of the phenol with the butadiene derivative is cyclized in the presence of a catalyst chosen from paratoluenesulphonic acid, scandium triflate, dichloromethylaluminium, ytterbium triflate, lanthanum triflate, tin(II) triflate, zinc chloride and dichloroethoxyaluminium. A derivative of the formula (VI)

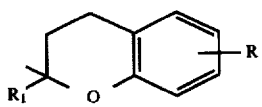
(VI)

is obtained in which $R_1$ represents an unsubstituted or substituted alkenyl or alkyl radical containing at least two carbon atoms, having the same meaning as in formula (II) and R represents the same radical(s) as in formula (I).

The derivative obtained may then be hydrogenated.

According to another preferred way of carrying out the invention, trimethylhydroquinone is condensed with β-springene to form the derivative of formula (V)

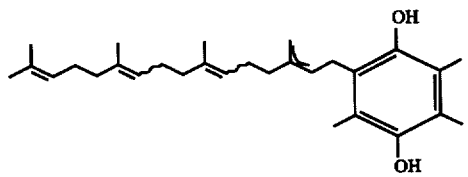
(V)

which is preferably cyclized with a catalyst chosen from dichloromethylaluminium and paratoluenesulphonic acid to give a compound of the formula (VI) having the structure (VII)

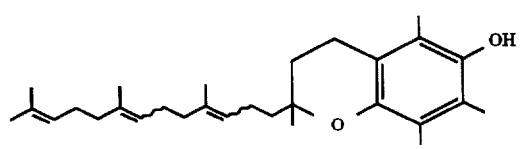
(VII)

which is then hydrogenated to produce vitamin E. The hydrogenation is preferably performed in the presence of a palladium-based catalyst. Tocopherol acetate, a commercial product, is then obtained by acetylation of the derivative obtained in the preceding step.

The invention will be described more fully with the aid of the following examples which should not be considered as limiting the invention.

EXAMPLES

During the following examples, the rate of conversion (RC) is understood to mean the ratio of the compound converted to the compound introduced. The yield is understood to mean the molar ratio of the product obtained to the product introduced. The yield is equal to the product of the rate of conversion and the yield over the product converted.

Experimental Procedure

The following were charged into a 50-ml reactor provided with magnetic stirring, a thermometer and a condenser:

15 mmol of diene 30 mmol of phenolic compound 3 mmol of potassium carbonate 0.45 mmol of diphenylphosphinobutane 0.15 mmol of $(RhClCOD)_2$ 15 ml of degassed toluene.

The mixture was purged with argon and then refluxed at 120° C. for 8 hours. The temperature was then brought down to 20° C. and the reaction medium was taken up in 15 ml of water and 15 ml of ethyl ether. The aqueous phase was washed with 15 ml of ethyl ether and the ethereal phases were combined, washed with 15 ml of water, dried over $MgSO_4$, filtered and concentrated.

The rate of conversion of the diene was quantitative (analysis by gas chromatography, by liquid chromatography, by thin-layer chromatography and by $^1H$ NMR). The excess phenolic compound was removed by washing with 1N sodium hydroxide. The excess phenolic compound could have been recycled by acid extraction.

| DIENE/PHENOLIC COMPOUND PAIRS | | | |
|---|---|---|---|
| Examples | DIENE | PHENOLIC COMPOUND | YIELD ISOLATED | TIME hours |
| 1 | Myrcene | trimethylhydroquinone | 85% | 8 |
| 2 | Myrcene | 2,3,5-trimethylphenol | 90% | 8 |
| 3 | Myrcene | 2,6-dimthylphenol | 74% | 8 |
| 4 | β-springene | trimethylhydroquinone | 85% | 8 |
| 5 | Myrcene | phenol | 72% | 8 |
| 6 | β-springene | 2,3,5-trimethylphenol | 67% | 8 |

| NATURE OF THE PHOSPHINE | | | |
|---|---|---|---|
| Examples | PHOSPHINE | QUANTITY | YIELD | TIME |
| 1 | $Ph_2P(CH_2)_4PPh_2$ | 3% | 84% | 8 hours |
| 7 | $Ph_2P(CH_2)_4PPh_2$ | 1.5% | RC (diene) = 50% | 8 hours |
| 8 | $Ph_2P(CH_2)_4PPh_2$ | 6% | 85% | 8 hours |
| C1 | $PPh_3$ | 6% | Traces of expected product | 24 hours |
| C2 | $PPh_3$ | 3% | Traces of expected product | 24 hours |

-continued

NATURE OF THE PHOSPHINE

| Examples | PHOSPHINE | QUANTITY | YIELD | TIME |
|---|---|---|---|---|
| C3 | (cyclohexyl)$_3$P  | 6% | Traces of expected product | 24 hours |
| C4 | P(PhSO$_3$Na)$_3$ | 2.7% | 0 | 24 hours |
| 9 | Ph$_2$P(CH$_2$)$_2$PPh$_2$ | 3% | 10% | 24 hours |
| 10 | Ph$_2$P(CH$_2$)$_6$PPh$_2$ | 3% | 20% | 24 hours |
| 11 | Ph$_2$P(CH$_2$)$_3$PPh$_2$ | 3% | 44% | 24 hours |
| 12 | Ph$_3$P-ferrocene 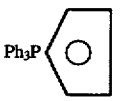 | 3% | 35% | 24 hours |
| 13 | bicyclic bis-PPh$_2$ 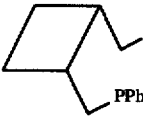 | 3% | 85% | 8 hours |

SOURCE OF RHODIUM

Example 1 was repeated using the following catalysts:

—[Rh Cl (P(C$_6$H$_5$)$_3$)$_2$]$_2$

—Rh Cl (CO)(P(C$_6$H$_5$)$_3$)$_2$

—[RH Cl (COD)]$_2$

The results of the condensation are expressed in the following table:

| | Myrcene + TMHQ | |
|---|---|---|
| (RhClCOD)$_2$ | 85% | 8 to 16 hours |
| RhCl(CO) (PPh$_3$)$_2$ | 85% | 12 hours |
| (RhCl(PPh$_3$)$_2$)$_2$ | 85% | 12 hours |

EXAMPLES 14 TO 24

VARIATION OF THE NATURE OF THE SOLVENT

| EXAMPLES | REAGENTS | SOLVENT | BASE | RESULT |
|---|---|---|---|---|
| 14 | Myrcene | H$_2$O 24 h at 120° C. | Buffer pH 10 or K$_2$CO$_3$ 1 eq | RY = 70% RC(Cg) = 72% |
| 15 | Myrcene | NMP 24h at 120° C. | 1 eq K$_2$CO$_3$ | RC = 28% |
| 16 | Myrcene | Toulene/H$_2$O 8/15 | Buffer pH 10 | RC(Cg) = 83% RY = 71% |
| 17 | Myrcene | NMP/H$_2$O 8/15 | Buffer pH 10 | RC(Cg) = 58% RY = 31% |
| 18 | Myrcene (2 eq TMHQ) | DME 17 h at 85° C. | 1 eq K$_2$CO$_3$ | RC(C$_{10}$) = 100% RY assayed ≈ 95% |
| 19 | β-springene + 2 eq TMHQ | DME 8 h at reflux | 0.2 eq | RY assayed < 20% |
| 20 | β-springene + 2 eq TMHQ | MIBK 8 h at reflux | 0.2 eq | RY assayed < 20% |
| 21 | β-springene + 2 eq TMHQ | IPAC 16 h at reflux | 0.2 eq | RY assayed = 80% |

EXAMPLES 22 to 25: Cyclization Test 25.2 g of C$_{29}$ phenolic derivative were used, which were obtained during the condensation of β-springene with trimethylhydroquinone and 1.58 ml of a molar solution, in hexane, of CH$_3$AlCl$_2$. The phenolic derivative in 20 ml of toluene was charged into a three-necked round-bottomed flask, under magnetic stirring, and the hexane solution of CH$_3$AlCl$_2$ was added. The mixture was allowed to react for 24 hours at room temperature and then it was heated under reflux. The cyclized derivative of formula (VII) was obtained with a yield of 78%. The product was purified by chromatography on silica and then it was hydrogenated in the presence of 2 mol % of Pd/C and then the hydrogenated derivative was acetylated in the presence of acetate anhydride, triethylamine and dimethylaminopyridine in hexane.

Tocopherol acetate was obtained with a yield of product isolated over the beta-springene introduced of 47%. The preceding example was repeated with cyclization catalysts of a different nature.

| EXAMPLES | Cyclization catalyst Molar ratio/C$_{29}$ | Yield of product of formula (VI) / (V) | Yield of tocopherol acetate/β-springene |
|---|---|---|---|
| 22 | CH$_3$AlCl$_2$[0.12] | 78% | 47% |
| 23 | Sc(CF$_3$SO$_3$)$_3$[0.12] | 67% | 22% |
| 24 | EtO AlCl$_2$[0.3] | 75% | 29% |
| 25 | paratoluenesulphonic acid [0.1] | 83% | 34% |

What is claimed is:

1. A process for preparing substituted phenols of formula (I)

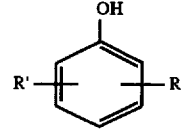

in which R represents one or more groups, which are identical or different and are selected from hydrogen, hydroxyl radicals and alkyl radicals having from 1 to 6 carbon atoms, and R' represents a radical selected from the radicals of formula (II)

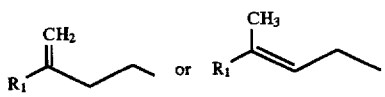

in which $R_1$ represents an unsubstituted or substituted alkylene or alkyl radical, wherein said radical of formula (II) contains at least 6 carbon atoms, which process comprises the step of:

condensing a phenol of formula (III)

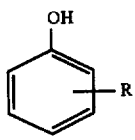

in which R has the same meaning as in formula (I), in a single-phase medium with a butadiene derivative of formula (IV)

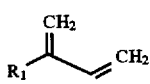

in which $R_1$ has the same meaning as in formula (II), and wherein said butadiene derivative contains at least 6 carbon atoms in the presence of a base, a diphosphine soluble in an aprotic organic solvent, and a catalyst based on rhodium with the oxidation number (+1).

2. A process according to claim 1, wherein said butadiene derivative of formula (IV) is selected from polyene compounds.

3. A process according to claim 2, wherein said butadiene derivative of formula (IV) is selected from myrcene, springene and farnesene.

4. A process according to claim 1, wherein said rhodium is an organic salt of rhodium selected from [Rh Cl (P(C$_6$H$_5$)$_3$)$_2$]$_2$, Rh Cl (CO) (P(C$_6$H$_5$)$_3$)$_2$ and [Rh Cl (COD)]$_2$.

5. A process according to claim 1, wherein said phenol of formula (III) is selected from trimethylphenol and tetramethylhydroquinone.

6. A process according to claim 1, wherein said diphosphine soluble in an aprotic organic solvent is selected from bidentate diphosphines having a hydrocarbon chain between the two phosphorus atoms comprising from 3 to 5 carbon atoms.

7. A process according to claim 6, wherein said diphosphine soluble in an aprotic organic solvent is a diphenylphosphinobutane of formula:

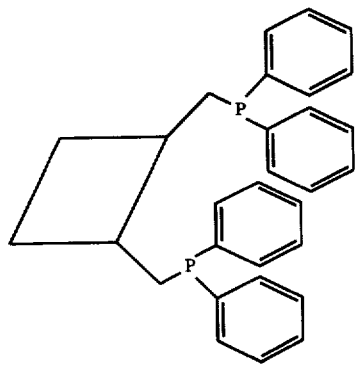

8. A process according to claim 6, wherein said diphosphine soluble in an aprotic organic solvent is selected from:

—1,4-bis(diphenylphosphino)butane,

—1,3-bis(diphenylphosphino)propane,

—1,2-bis(diphenylphosphinomethylene)cyclobutane, and

—1,5-bis(diphenylphosphino)pentane.

9. A process according to claim 1, for preparing a compound of formula (V)

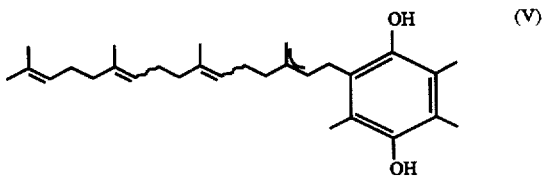

wherein in said condensing step, springene is condensed with trimethylhydroquinone in the presence of a diphosphine soluble in an aprotic organic solvent selected from bidentate diphosphines having a hydrocarbon chain between the two phosphorus atoms comprising from 3 to 5 carbon atoms and in the presence of (RhClCOD)$_2$ in toluene.

10. A process according to claim 1, wherein said phenol of formula (III) and said butadiene derivative of formula (IV) are contacted in a molar ratio of said butadiene derivative to said phenol ranging from 0.2 to 2.

11. A process according to claim 1, wherein in said condensing step, β-springene or myrcene is condensed with trimethylhydroquinone in the presence of a catalyst based on rhodium with an oxidation number (+1) and of bis(diphenylphosphino)butane or bis(diphenylphosphino)cyclobutane.

12. A process according to claim 1, wherein the molar ratio of said rhodium-based catalyst to said butadiene derivative ranges from 0.1% to 10%.

13. A process according to claim 1, wherein said aprotic organic solvent is toluene, dimethoxyethane or isopropyl acetate.

14. A process according to claim 1, wherein the reaction temperature of said process ranges from 30° C. to 150° C.

15. A process according to claim 1, wherein the reaction time of said process ranges from a few hours to one day.

16. A process according to claim 1, wherein said base is an alkali metal carbonate.

17. A process for preparing vitamin E, which comprises the steps of:

condensing a phenol of formula (III)

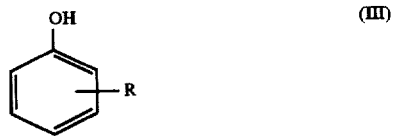

in which R represents one or more groups, which are identical or different and are selected from hydrogen, hydroxyl radicals and alkyl radicals having from 1 to 6 carbon atoms, in a single-phase medium with a butadiene derivative of formula (IV)

in which $R_1$ represents an unsubstituted or substituted alkylene or alkyl radical, and wherein said butadiene derivative contains at least 6 carbon atoms in the presence of a base, a diphosphine soluble in an aprotic organic solvent, and a catalyst based on rhodium with the oxidation number (+1) to form a substituted phenol of formula (I)

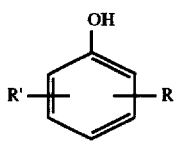 (I)

in which R represents one or more groups, which are identical or different and are selected from hydrogen, hydroxyl radicals and alkyl radicals having from 1 to 6 carbon atoms, and R' represents a radical selected from the radicals of formula (II)

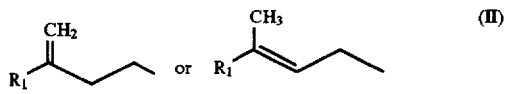 (II)

in which $R_1$ represents an unsubstituted or substituted alkylene or alkyl radical, wherein the radical of formula (II) contains at least 6 carbon atoms, cyclizing said substituted phenol of formula (I) in the presence of a catalyst selected from paratoluenesulphonic acid, scandium triflate, dichloromethylaluminium, ytterbium triflate, lanthanum triflate, tin(II) triflate, zinc chloride, and dichloroethoxyaluminium to obtain a derivative of formula (VI)

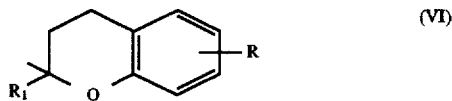 (VI)

in which $R_1$ represents an unsubstituted or substituted alkenyl or alkyl radical containing at least two carbon atoms, having the same meaning as in formula (II) above, and R represents the same radical(s) as in formula (I) above, and hydrogenating said cyclized compound.

18. A process for preparing vitamin E according to claim 17, wherein in said condensing step, trimethylhydroquinone is condensed with β-springene to form a substituted phenol derivative of formula (V)

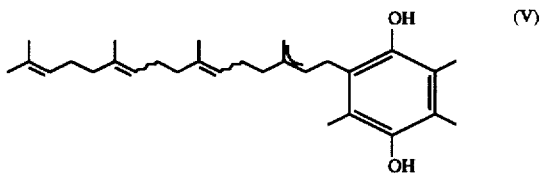 (V)

the substituted phenol derivative of formula (V) is cyclized in the presence of a catalyst selected from dichloromethylaluminium and paratoluenesulphonic acid to obtain a derivative of formula (VII)

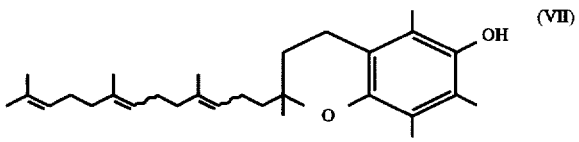 (VII)

and the cyclized derivative of formula (VII) is hydrogenated.

19. A process according to claim 18, wherein said hydrogenating step comprises a palladium-based catalyst.

20. A process according to claim 18, wherein said hydrogenated cyclized derivative is acetylated.

* * * * *